(12) United States Patent
Maso Sabaté et al.

(10) Patent No.: US 10,722,604 B2
(45) Date of Patent: Jul. 28, 2020

(54) DEVICE FOR RELEASING VOLATILE SUBSTANCES

(71) Applicant: ZOBELE HOLDING S.P.A., Trento (ES)

(72) Inventors: Jordi Maso Sabaté, Barcelona (ES); Cedric Gobber, Barcelona (ES); Joaquín Llorente Alonso, Barcelona (ES); Jordi Guiu Pont, Barcelona (ES)

(73) Assignee: ZOBELE HOLDING S.P.A., Trento (IT)

( * ) Notice: Subject to any disclaimer, the term of this patent is extended or adjusted under 35 U.S.C. 154(b) by 0 days.

(21) Appl. No.: 15/574,860

(22) PCT Filed: May 13, 2016

(86) PCT No.: PCT/EP2016/060847
§ 371 (c)(1),
(2) Date: Nov. 17, 2017

(87) PCT Pub. No.: WO2016/184807
PCT Pub. Date: Nov. 24, 2016

(65) Prior Publication Data
US 2018/0126023 A1  May 10, 2018

(30) Foreign Application Priority Data
May 18, 2015 (ES) .................................. 201530677

(51) Int. Cl.
*A61L 9/12* (2006.01)
*A61L 9/04* (2006.01)

(52) U.S. Cl.
CPC .................. *A61L 9/12* (2013.01); *A61L 9/048* (2013.01)

(58) Field of Classification Search
CPC .................................. A61L 9/12; A61L 9/048
(Continued)

(56) References Cited

U.S. PATENT DOCUMENTS

| 1,897,573 A | 2/1933 | Curran |
| 5,407,642 A * | 4/1995 | Lord .......................... A61L 9/12 239/55 |

(Continued)

FOREIGN PATENT DOCUMENTS

| EP | 0 841 070 A2 | 5/1998 |
| EP | 2 832 375 A1 | 2/2015 |

(Continued)

OTHER PUBLICATIONS

International Search Report dated Jul. 13, 2016 in corresponding PCT International Application No. PCT/EP2016/060852.
(Continued)

*Primary Examiner* — Christopher S Kim
(74) *Attorney, Agent, or Firm* — Ostrolenk Faber LLP

(57) ABSTRACT

A device for releasing volatile substances, including a container that contains a solid substrate impregnated with volatile substances and a clamping element. The device also includes at least two retaining arms of the solid substrate. The arms extend substantially from the center of the container and towards the larger exterior edge of the container. The device allows the deformation of the solid substrate to be contained since the arms force the solid substrate to maintain the position thereof in contact with the arms.

2 Claims, 1 Drawing Sheet

(58) Field of Classification Search
USPC .................................. 239/54, 55, 56, 57, 60
See application file for complete search history.

(56) References Cited

U.S. PATENT DOCUMENTS

| | | | |
|---|---|---|---|
| 5,422,078 A | 6/1995 | Colon | 422/123 |
| 6,071,529 A | 6/2000 | Ballard et al. | 424/408 |
| 2008/0087740 A1 | 4/2008 | Gusenoff et al. | 239/55 |
| 2015/0217017 A1* | 8/2015 | Venisti | A61L 9/12 |
| | | | 239/55 |

FOREIGN PATENT DOCUMENTS

| | | |
|---|---|---|
| ES | 2 145 985 T3 | 7/2000 |
| GB | 2492370 A | 1/2013 |
| KR | 20-0469969 Y1 | 11/2013 |
| WO | WO 03/003826 A2 | 1/2003 |
| WO | WO 2006/002395 A2 | 1/2006 |
| WO | WO 2007/125384 A2 | 11/2007 |
| WO | WO 2011/121360 A1 | 10/2011 |

OTHER PUBLICATIONS

Written Opinion dated Jul. 13, 2016 in corresponding PCT International Application No. PCT/EP2016/060852.
Search Report dated Oct. 18, 2016 in corresponding Spanish Patent Application No. 201530679.
International Search Report dated Jul. 14, 2016 in corresponding PCT International Application No. PCT/EP2016/060847.
Written Opinion dated Jul. 14, 2016 in corresponding PCT International Application No. PCT/EP2016/060847.
Search Report dated Nov. 11, 2016 in corresponding Spanish Patent Application No. 201530677.

* cited by examiner

DEVICE FOR RELEASING VOLATILE SUBSTANCES

CROSS-REFERENCE TO RELATED APPLICATIONS

The present application is a 35 U.S.C. § 371 national phase conversion of PCT/EP2016/060847, filed May 13, 2016, which claims priority to Spanish Patent Application No. P201530677, filed May 18, 2015. The entire contents of both applications are incorporated in full herein by reference. The PCT International Application was published in the English language.

DESCRIPTION

The present invention relates to a device for releasing volatile substances, in particular a device for vehicles having a gel deposit which limits the deformation of the gel during evaporation.

BACKGROUND OF THE INVENTION

The use of air fresheners for vehicles has been a growing market in recent years. There are different technologies for this application which are based on the same domestic use technologies. For example, devices with a bottle and a wick, membrane devices, etc., the majority with a clamping element to fix the device to the ventilation screen of the air conditioning system of the vehicle.

A technology which has been growing considerably recently consists of a system which has a solid gel which contains a volatile substance. This system has a minimal construction: an open container in which the gel has been poured prior to being made solid, a peelable barrier sheet to prevent the evaporation of the product prior to the first use and a clamping element.

The clamping element is often placed in the center of the container to allow the device to be assembled in the center of the screen. Thus the container has a central part, usually cylindrical in which the clamping element is fixed. This means that the device is sold with the clamping element unassembled in order to allow the removal of the barrier sheet.

A significant problem with the use of these types of devices based on gel is linked to the fact that the gel progressively contracts when the volatile substance is released. This contraction is not homogenous over the entire volume of the gel since only one side of the gel is exposed to the atmosphere, generally the rear part of the device, that is to say, the part that is oriented towards the ventilation screen. Thus, this side of the gel contracts first, which can cause the bending of the gel in the direction of the screen.

This is critical if the bending is so significant that the gel ends up contacting the plastic ventilation screen, or the dashboard of the vehicle since the most commonly used plastics for manufacturing the screen or the dashboard are selected for the mechanical and aesthetic characteristics thereof, but they have very poor resistance to perfumes.

Therefore, the contact between the gel and the plastic of the vehicle may cause discoloration of the plastic, the separation or the appearance of bubbles or creases in the coating of the plastic. If this occurs, the only solution is to replace the damaged parts which may be expensive.

This phenomenon is made even more difficult to solve because there are a very high number of usage configurations of the product since there are a wide number of designs of the screen, different ways of fixing the device on the same screen and different environmental conditions for the evaporation (heating, air conditions, ultraviolet light system, etc.).

Therefore, the object of the present invention is to provide a device for releasing volatile substances for vehicles having a gel deposit which limits the deformation of the gel during the evaporation.

DESCRIPTION OF THE INVENTION

Using the device for releasing volatile substances of the invention, the cited drawbacks can be resolved, presenting other advantages which are described below.

The device for releasing volatile substances according to the present invention comprises a container which contains a solid substrate impregnated with volatile substances and a clamping element and is characterized in that it also comprises at least two retaining arms of the solid substrate.

Owing to these arms, the deformation of the solid substrate is contained since they force said solid substrate to maintain the position thereof in contact with the arms.

Advantageously, said arms extend substantially from the center of the container and towards the larger exterior edge of the container.

According to a preferred embodiment, said arms are joined to the clamping element by means of an axis and said arms being substantially perpendicular to said axis.

Furthermore, the impregnated solid is preferably a gel.

According to alternative embodiments, said container has a rectangular longitudinal section and the arms extend from the center of the rectangle towards the smaller sides thereof or said container has a triangular longitudinal section and three arms extend from the center of the triangle towards the vertices thereof or said container has a quadrangular longitudinal section and four arms extend from the center of the square towards the vertices thereof.

BRIEF DESCRIPTION OF THE DRAWINGS

In order to better understand what has been stated, drawings are included in which a practical embodiment is depicted schematically and only as a non-limiting example.

DESCRIPTION OF A PREFERRED EMBODIMENT

Figure 1:
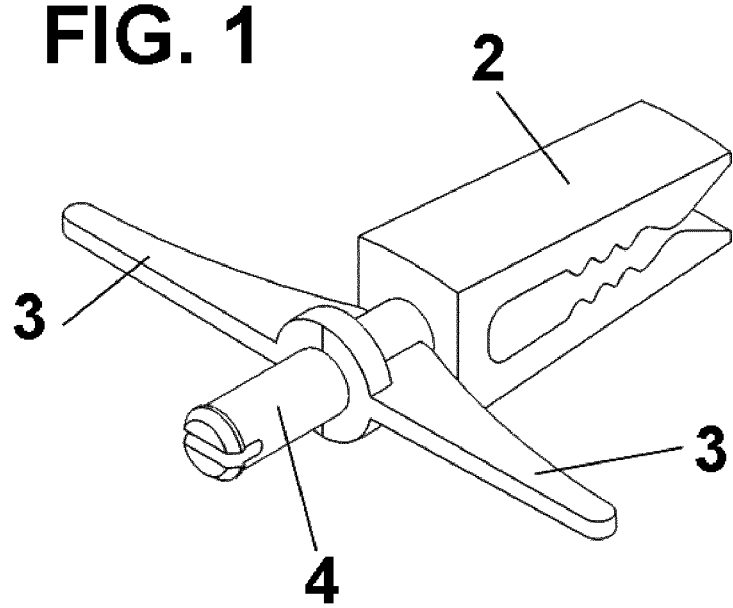
FIG. 1 is a perspective view of the clamping element and the arms which form part of the device for releasing volatile substances according to the present invention.
Figure 2:
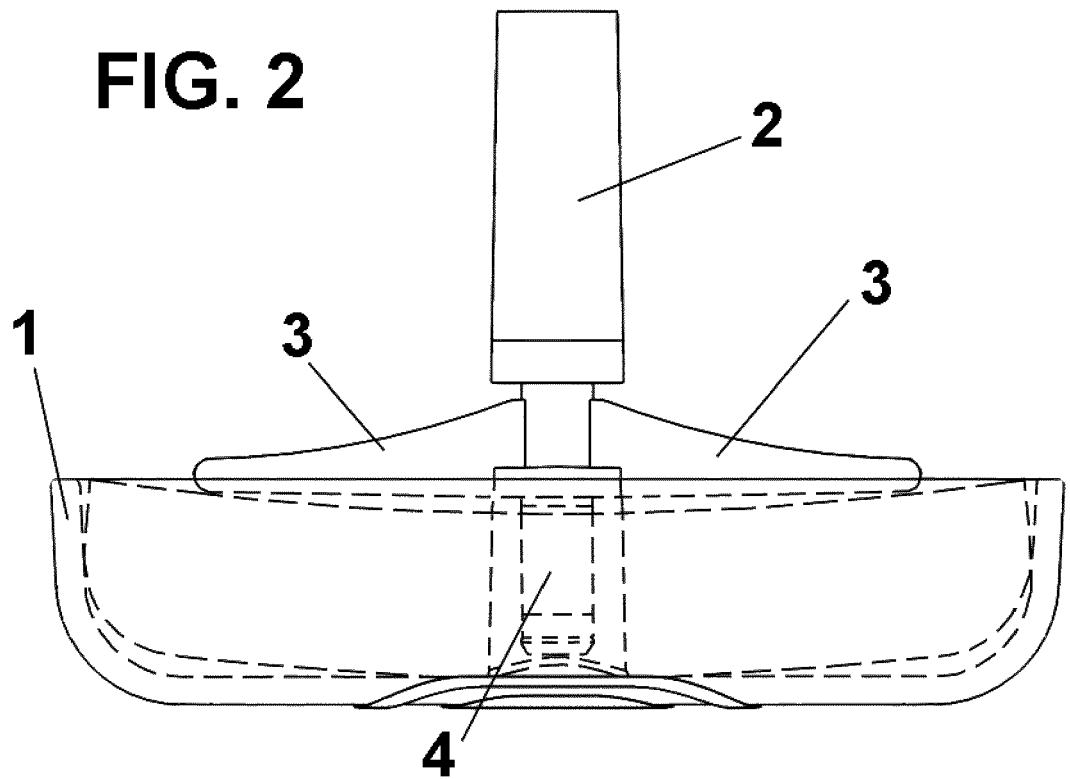
FIG. 2 is a plan view of the device for releasing volatile substances in which the contraction of the deposit during the use thereof has been depicted in dashed lines.

The device for releasing volatile substances according to the present invention comprises a container 1 for containing a solid substrate, for example a gel, impregnated with volatile substances, a clamping element 2 for the fixing thereof to, for example a ventilation screen of a vehicle and at least two retaining arms 3 of the solid substrate which can be housed at least partially in the interior of the container 1 and in contact with the solid substrate.

These three arms 3 limit the possible bending of the gel with a limited influence on the evaporation.

According to the embodiment depicted, said clamping element 2 is joined to the arms 3 by means of an axis 4 and said arms 3 are substantially perpendicular with respect to said axis 4.

According to the embodiment depicted, the arms 3 advantageously extend along the longitudinal axis of the container 1 to lock the movement of the gel when it contracts.

The number of arms 3 mainly depends on the geometry of the container 1. As the gel is locked from the axis 4, the arms 3 must lock the gel in the direction of the greatest distance from the axis 4 to the edge of the container 1.

Thus, in the case of a container 1 with a longitudinal design, for example substantially rectangular, only two arms 3 will be necessary.

In the case of a container 1 with a triangular design, three arms 3 aligned in the direction between the center and the vertices of the triangle will be necessary.

In the case of a container 1 with a square design, four arms 3 will be necessary, extending from the center towards the vertices of the square.

It must be indicated that for other types of shapes, it is envisaged that four arms 3 will be sufficient to solve the contraction problem since an excessive number of arms may present the drawback of covering the gel too much and thus reducing the evaporation.

The arms 3 have a minimum thickness for mechanically supporting the deformation of the gel, the thickness thereof being approximately 2 to 3 mm.

The length of the arms 3 can be extended along the entire dimension of the container, that is to say, to the exterior edges or vertices, although it is sufficient to cover only 80% of this distance, that is to say, they can approach the edge or vertex, but leave a separation. In fact, the length of the arms 3 will be the length necessary for preventing the bending level of the gel exceeding the external perimeter plane of the container 1.

In this way, the bending problem of the gel during the contraction thereof is resolved in a very simple and low-cost manner, simply by adding the arms 3 and without having to modify the design of any other components thereof.

In spite of the fact that reference has been made to a specific embodiment of the invention, it is evident for a person skilled in the art that the device for releasing volatile substances described is capable of undergoing numerous variations and modifications and that all the details mentioned can be substituted for others which are technically equivalent without departing from the scope of protection defined by the attached claims.

The invention claimed is:

1. A volatile substance releasing device comprising:
    a container containing a solid substrate that is a gel impregnated with a volatile substance;
    a clamping element;
    at least two retaining arms configured to retain the gel; and
    a central body positioned on an axis substantially perpendicular to said arms and configured to join said retaining arms to the clamping element, wherein a first arm of the at least two arms has a longitudinal extent from the central body in a first direction, and a second arm of the at least two arms has a longitudinal extent from the central body in a second direction away from the first direction,
    wherein the retaining arms directly contact the gel on a side of the gel facing the clamping element, wherein the retaining arms lock the gel at a side of the container facing the clamping element.

2. The device according to claim 1, wherein each arm of the at least two retaining arms extends substantially from the center body towards an exterior edge or of the container.

\* \* \* \* \*